United States Patent
Prenveille

(10) Patent No.: US 10,517,243 B2
(45) Date of Patent: Dec. 31, 2019

(54) PEPPER VARIETY NUN 70048 PPH

(71) Applicant: Nunhems B.V., AB Nunhem (NL)

(72) Inventor: Baptiste AndréÉmile Prenveille, Culiacan (MX)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 15/900,981

(22) Filed: Feb. 21, 2018

(65) Prior Publication Data

US 2018/0160640 A1 Jun. 14, 2018

Related U.S. Application Data

(60) Provisional application No. 62/522,135, filed on Jun. 20, 2017.

(51) Int. Cl.

| | |
|---|---|
| *A01H 5/10* | (2018.01) |
| *A01H 1/06* | (2006.01) |
| *A01H 5/08* | (2018.01) |
| *C12N 15/01* | (2006.01) |
| *A01H 1/02* | (2006.01) |
| *A01H 4/00* | (2006.01) |
| *A01H 6/82* | (2018.01) |

(52) U.S. Cl.
CPC .............. *A01H 1/06* (2013.01); *A01H 1/02* (2013.01); *A01H 1/025* (2013.01); *A01H 4/005* (2013.01); *A01H 5/08* (2013.01); *A01H 5/10* (2013.01); *A01H 6/822* (2018.05); *C12N 15/01* (2013.01)

(58) Field of Classification Search
None
See application file for complete search history.

(56) References Cited

U.S. PATENT DOCUMENTS

| 8,492,619 B2 | 7/2013 | Bar et al. | |
|---|---|---|---|
| 2006/0037100 A1 | 2/2006 | Kim et al. | |
| 2011/0258744 A1* | 10/2011 | Todd, Jr. | A01H 5/02 800/317.1 |
| 2015/0059012 A1* | 2/2015 | Saldivar | A01H 5/08 800/260 |

FOREIGN PATENT DOCUMENTS

| WO | 2013182646 A1 | 12/2013 |
|---|---|---|
| WO | 2013078319 A1 | 5/2014 |
| WO | 2014076249 A1 | 5/2014 |

OTHER PUBLICATIONS

Poehlman et al., 1995, Methods in Plant Breeding IV, Iowa State Press; selected pp. 157-180.*
Sang-Gu, Kim, et al., Callus growth and plant regeneration in diverse cultivars of cucumber (*Cucumis sativus* L.), Plant Cell, Tissue and Organ Culture, 1988, pp. 67-74, vol. 12.
Martin, Eugenia, et al., Identification of markers linked to agronomic traits in globe artichoke, Australian Journal of Crop Science, 2008, pp. 43-46, vol. 1, No. 2.
Parvathaneni, Rajiv Krishna, et al., Fingerprinting in Cucumber and Melon (*Cucumis* spp.) Genotypes Using Morphological and ISSR Markers, J. Crop Sci. Biotech., 2011, pp. 39-43, vol. 14, No. 1.
Wijnker, Erik, et al., Hybrid recreation by reverse breeding in *Arabidopsis thaliana*, Nature Protocols, 2014, pp. 761-772, vol. 9.
Vos, Pieter, et al., AFLP: a new technique for DNA fingerprinting, Nucleic Acids Research, 1995, pp. 4407-4414, vol. 23 No. 21.
Guidelines for the Conduct of Tests for Distinctness, Uniformity and Stability, TG/76/8 (Geneva, 2006—updated 2015), as published by UPOV (International Union for the Protection of New Varieties and Plants: upov.int/ under edocs/ tgdocs/en/tg076.pdf.
US Department of Agriculture, Agricultural Marketing Service, Plant Variety Protection Office, Beltsville, MD: ams.usda.gov/sites/defaultfiiles/media/56-Pepper.pdf. (date not specified).
Tiwari, Aparna, et al., Parthenocarpic potential in *Capsicum annuum* L. is enhanced by carpelloid structures and controlled by a single recessive gene, BMC Plant Biology, 2011, vol. 11:143.
Kothari, S.L., et al., Chilli peppers—A review on tissue culture and transgenesis, Biotechnology Advances, 2010, p. 35-48, vol. 28.

* cited by examiner

*Primary Examiner* — Bratislav Stankovic
(74) *Attorney, Agent, or Firm* — Arent Fox LLP

(57) ABSTRACT

The invention provides a new and distinct hybrid variety of pepper, NUN 70048 PPH as well as seeds and plants and fruits thereof.

23 Claims, No Drawings

PEPPER VARIETY NUN 70048 PPH

CROSS-REFERENCE TO RELATED APPLICATIONS

The present application claims the benefit of U.S. Patent Application Ser. No. 62/522,135, filed 20 Jun. 2017, which is incorporated herein by reference in its entirety.

FIELD OF THE INVENTION

The present invention relates to the field of plant breeding and, more specifically, to the development of NUN 70048 PPH (also designated as NUN 70048 or NUN 70048 F1 or NUN 70048 hybrid). The invention further relates to vegetative reproductions of NUN 70048 PPH, methods for tissue culture of NUN 70048 PPH and regenerating a plant from such a tissue culture and also to phenotypic variants of NUN 70048 PPH.

The goal of vegetable breeding is to combine various desirable traits in a single variety/hybrid. Such desirable traits may include greater yield, resistance to diseases, insects or other pests, tolerance to heat and drought, better agronomic quality, higher nutritional value, enhanced growth rate and improved fruit properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype. Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, and the evaluation of the hybrids resulting from the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential.

One crop species which has been subject to such breeding programs and is of particular value is the pepper. Pepper (*Capsicum* spp.) is naturally a diploid and the basic chromosome number of the genus is x=12, most are 2n=2x=24, including the cultivated ones. A few wild species have 2n=26. Ploidy changes (both tetraploidy and haploidy) are relatively easy to induce in *Capsicum* species. Doubled haploids have proved particularly valuable in the analysis of the genetically complex basis of some resistances to pests and diseases.

The genus *Capsicum* originated in American tropics. The fruit of most species of *Capsicum* produce a strong burning sensation (pungency or spiciness) in the mouth of the unaccustomed eater due to the presence of capsaicin (methyl vanillyl nonenamide), a lipophilic chemical. Capsaicin can be present in large quantities in the placental tissue (which holds the seeds), the internal membranes, and to a lesser extent, the other fleshy parts of the fruits of plants in this genus. The seeds themselves do not produce any capsaicin. The amount of capsaicin in the fruit is highly variable and dependent on genetics and environment, giving almost all types of *Capsicum* varied amounts of perceived heat. The most recognizable *Capsicum* without capsaicin is the bell pepper, a cultivar of *Capsicum annuum*, which has a zero rating on the Scoville scale. The lack of capsaicin in bell peppers is due to a recessive gene that eliminates capsaicin and, consequently, the "hot" taste usually associated with the rest of the *Capsicum* family.

Many of the peppers currently used which are used in the fresh of processed marked in the United States are seeded hybrid varieties. Hybrid varieties offer the advantages of easy combination of dominant and recessive traits, such as disease resistance, from a set of inbred parents, as well as careful control of parentage. Many different pepper cultivars have been produced, and pepper breeding efforts have been underway in many parts of the world. Some breeding objectives include varying the color, texture and flavor of the fruit. Other objectives include disease or pest resistance, optimizing flesh thickness, yield, suitability to various climatic circumstances, heat, solid content (% dry matter), and sugar content.

Advances in biotechnology have also resulted in genetically engineered pepper plants with improved traits. For example, fungal resistant pepper plants comprising a PepEST or PepDef gene where the expression of the nucleic acid sequence in the plant resulted in increased resistance to fungal infection (see e.g. US application 20060037100, Feb. 16, 2006).

While breeding efforts to date have provided a number of useful pepper varieties with beneficial traits, there remains a great need in the art for new varieties with further improved traits. Such plants would benefit farmers and consumers alike by improving crop yields and/or quality.

SUMMARY OF THE INVENTION

In an aspect of the invention, a seed of pepper variety NUN 70048 PPH is provided, wherein a representative sample of said seed is deposited under Accession Number NCIMB43509. The invention also provides for a plurality of seeds of NUN 70048 PPH. The pepper seed of NUN 70048 PPH may be provided as an essentially homogeneous population of pepper seed. Therefore, seed of the invention may be defined as forming at least about 97% of the total seed, including at least about 98%, 99% or more of the seed. The population of seed of NUN 70048 PPH may be particularly defined as being essentially free from other seed. The seed population may be grown into plants to provide an essentially homogeneous population of pepper plants according to the invention.

Also encompassed is a plant grown from a seed of pepper variety NUN 70048 PPH and a plant part thereof. In another aspect the invention provides for a hybrid variety of pepper called NUN 70048 PPH. The invention also provides for a progeny of NUN 70048 PPH. Especially, a plant or a progeny retaining all or all but one, two or three of the "distinguishing characteristics" or all or all but one, two or three of the "morphological and physiological characteristics" of NUN 70048 PPH referred to herein, is encompassed herein as well as methods for producing that plant or progeny.

In one aspect, a plant or a progeny of the invention have all the physiological and morphological characteristics of variety NUN 70048 PPH when grown under the same environmental conditions. In another aspect such a plant or such progeny have all or all but one, two or three of the physiological and morphological characteristics of NUN 70048 PPH when measured under the same environmental conditions and evaluated at significance levels of 1%, 5% or 10% significance (which can also be expressed as a p-value) wherein a representative sample of seed of variety NUN 70048 PPH is deposited under Accession Number NCIMB 43509. In a second aspect, a plant or a progeny of the invention have all the physiological and morphological characteristics of variety NUN 70048 PPH when grown under the same environmental conditions. In another aspect such a plant or such progeny have all or all but one, two or three of the physiological and morphological characteristics as listed in Table 1 and/or 2 for variety NUN 70048 PPH when measured under the same environmental conditions and evaluated at significance levels of 1%, 5% or 10% significance.

In another aspect a plant of NUN 70048 PPH or said progeny plants has 7, 8, or more or all of the distinguishing characteristics: 1) Average fruit length; 2) Average fruit diameter at mid-point; 3) Average fruit diameter at calyx attachment; 4) Average number of flowers per leaf axil; 5) Typical plant attitude; 6) Average leaf width; 7) Average seed cavity length; 8) Average seed cavity diameter; 9) Average plant width; and 10) Fruit anthocyanin type. NUN 70048 PPH is a jalapeno-type hot pepper.

Also a plant part obtained from variety NUN 70048 PPH is provided, wherein said plant part is selected from the group consisting of: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said varieties, hypocotyl, cotyledon, a scion, a stock, a rootstock, a pistil, an anther, and a flower or a part thereof. Fruits are particularly important plant parts. In a further embodiment, the plant part obtained from variety NUN 70048 PPH is a cell, optionally a cell in a cell or tissue culture. That cell may be grown into a plant of NUN 70048 PPH.

The invention also provides a cell culture of NUN 70048 PPH and a plant regenerated from NUN 70048 PPH, which plant has all the characteristics of NUN 70048 PPH when grown under the same environmental conditions, as well as methods for regenerating NUN 70048 PPH. Alternatively, a regenerated plant may have one characteristic that is different from NUN 70048 PPH.

Further, a vegetatively propagated plant of variety NUN 70048 PPH is provided having all or all but one, two or three of the morphological and physiological characteristics NUN 70048 PPH when grown under the same environmental conditions.

Further, a pepper fruit produced on a plant grown from a seed of NUN 70048 PPH is provided.

In still another aspect, a seed growing or grown on a plant of NUN 70048 PPH is provided (i.e. produced after pollination of the flower of NUN 70048 PPH).

DEFINITIONS

All patent and non-patent documents cited herein are incorporated by reference in their entirety.

"Pepper" refers herein to plants of the species *Capsicum annuum* or *frutescens*, and fruits thereof. The most commonly eaten part of a pepper is the fruit or berry. The fruit comprises a stem or peduncle or pedicel, calyx, placenta, fruit wall, veins, shoulder, base, apex, locule or lobe, septa, exocarp, mesocarp, endocarp, pericarp, optionally secondary peppers, optionally capsaicin glands and optionally seed. The stem or peduncle or pedicel, calyx, placenta, fruit wall, veins, shoulder, base, apex, locule or lobe, septa, exocarp, mesocarp, endocarp, pericarp, secondary peppers, capsaicin glands and seedcoat of the seed are maternal tissues, that is they are genetically identical to the plant on which they grow.

"Cultivated pepper" refers to plants of *Capsicum annuum*, or a closely related species, i.e. varieties, breeding lines or cultivars of the species *C. annuum* as well as crossbreds thereof, or crossbreds with other *Capsicum* species, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of *Capsicum* and related species.

"Hot pepper" refers to peppers that have high pungency, i.e. high amounts of capsaicin.

The terms "pepper plant designated NUN 70048 PPH", "NUN 70048 PPH", "NUN 70048", "NUN 70048 F1", "70048 PPH" or "pepper 70048" are used interchangeably herein and refer to a pepper plant of variety NUN 70048 PPH, representative seed of which is deposited under Accession Number NCIMB 43509.

A "seed of NUN 70048 PPH" refers to a pepper seed which can be grown into a plant of NUN 70048 PPH wherein a representative sample of viable seed of NUN 70048 PPH is deposited under Accession Number NCIMB 43509. A seed can be in any stage of maturity, for example a mature, viable seed, or an immature, non-viable seed. A seed comprises an embryo and maternal tissues.

An "embryo of NUN 70048 PPH" refers to an "F1 hybrid embryo" as present in a seed of NUN 70048 PPH, a representative sample of said seed of NUN 70048 PPH is deposited under Accession Number NCIMB 43509.

A "seed grown on NUN 70048 PPH" refers to a seed grown on a mature plant of NUN 70048 PPH or inside a fruit of NUN 70048 PPH. The "seed grown on NUN 70048 PPH" contains tissues and DNA of the maternal parent, NUN 70048 PPH. The "seed grown on NUN 70048 PPH" contains an F2 embryo. When said seed is planted, it grows into a first generation progeny plant of NUN 70048 PPH.

A "fruit of NUN 70048 PPH" refers to a fruit containing maternal tissues of NUN 70048 PPH as deposited under Accession Number NCIMB 43509. In one option, the fruit contains seed grown on NUN 70048 PPH. In another option, the fruit does not contain seed, i.e. the fruit is parthenocarpic. The skilled person is familiar with methods for inducing parthenocarpy. Those methods comprise chemically or genetically inducing parthenocarpy. Compounds suitable for chemically inducing parthenocarpy include auxins, gibberellins and cytokinins. Genetic parthenocarpy can among others be induced by CaARF8 mutants (Tiwari et al., *BMC Plant Biology* 201111:143 DOI: 10.1186/1471-2229-11-143) or as in WO 2013078319 or U.S. Pat. No. 8,492, 619. A fruit can be in any stage of maturity.

Tissue culture" refers to a composition comprising isolated cells of the same or a different type or a collection of such cells organized into parts of a plant. Tissue culture of various tissues of pepper and regeneration of plants therefrom is well known and widely published (see, e.g., Sang-Gu et al. (1988), Plant Cell, Tissue and Organ Culture 12: 67-74; Kothari et al., (2010) Biotechnology Advances 28: 35-48. Similarly, the skilled person is well-aware how to prepare a "cell culture".

"UPOV descriptors" are the plant variety descriptors described for pepper in the "Guidelines for the Conduct of Tests for Distinctness, Uniformity and Stability, TG/76/8 (Geneva, 2006—updated 2015), as published by UPOV (International Union for the Protection of New Varieties and Plants, available on the world wide web at upov.int) and which can be downloaded from the world wide web at upov.int/under edocs/tgdocs/en/tg076.pdf and is herein incorporated by reference in its entirety.

"USDA descriptors" are the plant variety descriptors for pepper (Objective description of variety *Capsicum* spp.) as published by the US Department of Agriculture, Agricultural Marketing Service, Plant Variety Protection Office, Beltsville, Md. 20705 (available on the world wide web at ams usda.gov) and which can be downloaded from the world wide web atams.usda.gov/sites/default/files/media/56-Pepper.pdf. "Non-USDA descriptors" are other descriptors suitable for describing pepper.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS color chart: 2007 (The Royal Horticultural Society, charity No: 222879, PO Box 313 London SW1P2PE.

As used herein and except as otherwise indicated, the term "plant" includes the whole plant or any part thereof, preferably having the same genetic makeup as the plant from which it is obtained, such as a plant organ (e.g. harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, or parts of a plant (e.g. harvested tissues or organs), such as a fruit, a harvested fruit, a part of a fruit, a leaf, a part of a leaf, pollen, an ovule, an embryo, a petiole, a shoot or a part thereof, a stem or a part thereof, a root or a part thereof, a root tip, a cutting, a seed, a part of a seed, seed coat or another maternal tissue which is part of a seed grown on a variety of the invention, hypocotyl, cotyledon, a scion, a graft, a stock, a rootstock, a pistil, an anther, and a flower or parts of any of these and the like. Also any developmental stage is included, such as seedlings, cuttings prior or after rooting, mature plants or leaves. Alternatively, a plant part may also include a plant seed which comprises one or two sets of chromosomes derived from the parent plant, e.g. from NUN 70048 PPH. An F2 progeny produced from self-pollination of NUN 70048 PPH will thus comprise two sets of chromosomes derived from NUN 70048 PPH, while an F2 progeny derived from cross-fertilization of NUN 70048 PPH will comprise only one set of chromosomes from NUN 70048 PPH and the other set of chromosomes from the other parent.

"Harvested plant material" refers herein to plant parts (e.g. fruits detached from the whole plant) which have been collected for further storage and/or further use.

"Reference Variety" or "check variety" refers herein to variety 5810, a commercial variety from company *Seminis*, which has been planted in a trial together with NUN 70048 PPH. USDA descriptors of NUN 70048 PPH were compared to the USDA descriptors of 5810.

"Rootstock" or "stock" refers to the plant selected for its roots, in particular for the resistance of the roots to diseases or stress (e.g. heat, cold, salinity etc.). Normally the quality of the fruit of the plant providing the rootstock is less important.

"Scion" refers to a part of the plant that is attached to the rootstock. This plant is selected for its stems, leaves, flowers, or fruits. The scion contains the desired genes to be duplicated in future production by the stock/scion plant and may produce the desired pepper fruit.

"Stock/scion" or grafted plant refers to a pepper plant comprising a rootstock from one plant grafted to a scion from another plant.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g. the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Table 1 and/or 2 or "all or all but one, two or three of the physiological and morphological characteristics" of Table 1 and/or 2.

The physiological and/or morphological characteristics mentioned above are commonly evaluated at significance levels of 1%, 5% or 10% if they are numerical, or for having an identical degree (or type) if not numerical, if measured under the same environmental conditions. For example, a progeny plant or a Single Locus Converted plant or a mutated plant of NUN 70048 PPH may have one or more (or all) of the essential physiological and/or morphological characteristics of said variety listed in Table 1 and/or 2, as determined at the 5% significance level (i.e. $p<0.05$) when grown under the same environmental conditions.

"Distinguishing characteristics" or "distinguishing morphological and/or physiological characteristics" refers herein to the characteristics which distinguish (i.e. are different) between the new variety and other pepper varieties, such as the Reference Variety, when grown under the same environmental conditions. The distinguishing characteristics between NUN 70048 PPH and Reference Variety are described elsewhere herein and also can be seen in Table 1 and/or Table 2. When comparing NUN 70048 PPH with different varieties, the distinguishing characteristics will be different. In one aspect, the distinguishing characteristics may therefore include at least one, two, three or more (or all) of the characteristics listed in Table 1 and/or 2. All numerical distinguishing characteristics are statistically significantly different at $p<0.05$ between NUN 70048 PPH and the other variety, e.g. Reference Variety.

NUN 70048 PPH has the following distinguishing characteristics when compared to the Reference Variety: 1) Average fruit length; 2) Average fruit diameter at mid-point; 3) Average fruit diameter at calyx attachment; 4) Average number of flowers per leaf axil; 5) Typical plant attitude; 6) Average leaf width; 7) Average seed cavity length; 8) Average seed cavity diameter; 9) Average plant width; and 10) Fruit anthocyanin type. This can be seen in Table 1, where the USDA characteristics of NUN 70048 PPH are compared to the characteristics of Reference Variety, when grown under the same environmental conditions Thus, a pepper plant "comprising the distinguishing characteristics of NUN 70048 PPH (such as a progeny plant) refers herein to a plant which does not differ significantly from said variety in the distinguishing characteristics above. Therefore in one aspect a plant (such as a progeny plant of NUN 70048 PPH) is provided which does not differ significantly from NUN 70048 PPH in the distinguishing characteristics above.

Similarity and differences between two different plant lines or varieties can be determined by comparing the number of morphological and/or physiological characteristics (e.g. the characteristics as listed in Table 1 and/or 2) that are the same (i.e. statistically not significantly different) or that are different (i.e. statistically significantly different) between the two plant lines or varieties when grown under the same environmental conditions. A numerical characteristic is considered to be "the same" when the value for a numeric characteristic is not significantly different at the 1% ($p<0.01$) or 5% ($p<0.05$) significance level, using one way Analysis of variance (ANOVA), a standard method known to the skilled person. Non-numerical or "degree" or "type" characteristic are considered "the same" when the values have the same "degree" or "type" when scored using USDA and/or UPOV descriptors, if the plants are grown under the same environmental conditions.

As used herein, the term "variety", "cultivated pepper" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

A "plant line" is for example a breeding line which can be used to develop one or more varieties. A breeding line is typically highly homozygous.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean a method of taking a part of a plant and allowing that plant part to form at least roots, and also refer to the plant or plantlet obtained by that method. Optionally, the vegetative propagation is grown into a mature plant. The skilled person is aware of what plant parts are suitable for use in the method.

"Selfing" refers to self-pollination of a plant, i.e., the transfer of pollen from the anther to the stigma of the same plant.

"Crossing" refers to the mating of two parent plants. The term encompasses "cross-pollination" and "selfing".

"Cross-pollination" refers to the fertilization by the union of two gametes from different plants.

"Yield" means the total weight of all pepper fruits harvested per hectare of a particular line or variety. It is understood that "yield" expressed as weight of all pepper fruits harvested per hectare can be obtained by multiplying the number of plants per hectare times the "yield per plant". "Marketable yield" means the total weight of all marketable pepper fruits, especially fruit that is not cracked, damaged or diseased, harvested per hectare of a particular line or variety.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

"Harvest maturity" is referred to as the stage at which a pepper fruit is ripe or ready for harvest or the optimal time to harvest the fruit for the market, for processing or for consumption. In one embodiment, harvest maturity is the stage which allows proper completion of the normal ripening.

"Flavor" refers to the sensory impression of a food or other substance, especially a pepper fruit or fruit part (fruit flesh) and is determined mainly by the chemical senses of taste and smell. Flavor is influenced by texture properties and by volatile and/or non-volatile chemical components (organic acids, lipids, carbohydrates, sugars, salts etc.).

The term "traditional breeding techniques" encompasses herein crossing, selfing, selection, doubled haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one pepper line or variety to another. It optionally includes epigenetic modifications.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 70048 PPH. A progeny may be obtained by regeneration of cell culture or tissue culture or parts of a plant of said variety or selfing of a plant of said variety or by producing seeds of a plant of said variety. In further embodiments, progeny may also encompass plants obtained from crossing of at least one plant of said variety with another pepper plant of the same variety or another variety or (breeding) line, or with wild pepper plants. A progeny may comprise a mutation or a transgene. A "first generation progeny" is the progeny directly derived from, obtained from, obtainable from or derivable from the parent plant by, e.g., traditional breeding methods (selfing and/or cross-pollinating) or regeneration. Thus, a plant of NUN 70048 PPH is the male parent, the female parent or both of a first generation progeny of NUN 70048 PPH, or the progeny is regenerated from a cell or a plant part of variety NUN 70048 PPH. Progeny may have all the physiological and morphological characteristics of variety NUN 70048 PPH when grown under the same environmental conditions and/or progeny may have (be selected for having) one or more of the distinguishing characteristics of pepper of the invention. Using common breeding methods such as backcrossing or recurrent selection, one or more specific characteristics may be introduced into said variety, to provide or a plant comprising all but 1, 2, or 3 or more of the morphological and physiological characteristics of NUN 70048 PPH (as listed in Table 1 and/or 2)

The terms "gene converted" or "conversion plant" or "single locus converted plant" in this context refer to pepper plants which are developed by backcrossing wherein essentially all of the desired morphological and physiological characteristics of the parent variety or line are recovered, in addition to the one or more genes transferred into the parent via the backcrossing technique (optionally including reverse breeding or reverse synthesis of breeding lines) or via genetic engineering or through mutation breeding. Likewise a "Single Locus Converted (Conversion) Plant" refers to plants which are developed by plant breeding techniques comprising or consisting of mutation and/or by genetic transformation and/or by backcrossing, wherein essentially all of the desired morphological and physiological characteristics of a pepper variety are recovered in addition to the characteristics of the single locus having been transferred into the variety via the backcrossing technique. In case of a hybrid, the gene may be introduced in the male or female parental line.

"Marker" refers to a readily detectable phenotype, preferably inherited in codominant fashion (both alleles at a locus in a diploid heterozygote are readily detectable), with no environmental variance component, i.e., a heritability of 1.

"Average" refers herein to the arithmetic mean.

The term "mean" refers to the arithmetic mean of several measurements. The skilled person understands that the appearance of a plant depends to some extent on the growing conditions of said plant. Thus, the skilled person will know typical growing conditions for peppers described herein. The mean, if not indicated otherwise within this application, refers to the arithmetic mean of measurements on at least 10 different, randomly selected plants of a variety or line.

DETAILED DESCRIPTION

The present invention relates to a plant of NUN 70048 PPH wherein a representative sample of seeds of said variety is deposited under the Budapest Treaty, with Accession number NCIMB 43509.

The present invention also relates to a seed of pepper variety, referred to as NUN 70048 PPH, wherein a representative sample of said seed is deposited under the Budapest Treaty, with Accession number NCIMB 43509.

In another aspect, the invention provides for a pepper plant part of variety NUN 70048 PPH, preferably a fruit, a representative sample of seed from said variety is deposited under the Budapest Treaty, with Accession number NCIMB 43509.

A seed of hybrid variety NUN 70048 PPH is obtainable by crossing the male parent of said variety with the female parent of said variety and harvesting the seeds produced on the female parent. The resultant seeds of said variety can be grown to produce plants of said variety. In one embodiment a seed or a plurality of seeds of said variety are packaged into a container of any size or type (e.g., bags, cartons, cans, etc.). The seed may be disinfected, primed and/or treated with various compounds, such as seed coatings or crop protection compounds. The seed produces a plant of NUN 70048 PPH.

Also provided is a plant of pepper variety NUN 70048 PPH, or a fruit or other plant part thereof, produced from a seed, wherein a representative sample of said seeds is deposited under the Budapest Treaty, with Accession Number NCIMB 43509.

Also a plant part obtained from variety NUN 70048 PPH is provided, wherein said plant part is selected from the group consisting of: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said varieties, hypocotyl, cotyledon, a scion, a stock, a rootstock, a pistil, an anther, and a flower or a part thereof. Fruits are particularly important plant parts. Fruits may be parthenocarpic, or seedless, or contain immature and/or nonviable seeds. In a further embodiment, the plant part obtained from variety NUN 70048 PPH is a cell, optionally a cell in a cell or tissue culture. That cell may be grown into a plant of NUN 70048 PPH. A part of a variety of the invention, i.e. NUN 70048 PPH (or of progeny NUN 70048 PPH or of a plant having all physiological and/or morphological characteristics but one, two or three which are different from those of NUN 70048 PPH) further encompasses any cells, tissues, organs obtainable from the seedlings or plants in any stage of maturity.

The invention also provides for a food or feed product or a processed product comprising or consisting of a plant part described herein wherein the plant part can be identified as a part of the plant of the invention. Preferably, the plant part is a pepper fruit or part thereof and/or an extract from a fruit or another plant part described herein comprising at least one cell of NUN 70048 PPH. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

Such a plant part of NUN 70048 PPH can be stored and/or processed further. Encompassed are therefore also food or feed products comprising one or more of such parts, such as canned, chopped, cooked, roasted, in a sauce, in a sandwich, pasted, puréed or concentrated, juiced, frozen, dried, pickled, or powdered pepper fruit from NUN 70048 PPH or from progeny of said varieties, or from a derived variety, such as a plant having all but one, two or three physiological and/or morphological characteristics of NUN 70048 PPH.

In a preferred embodiment, the invention provides for a pepper fruit of variety NUN 70048 PPH, or a part of a fruit of said varieties. The fruit can be in any stage of maturity, for example immature or mature. In another embodiment, the invention provides for a container comprising or consisting of a plurality of harvested pepper fruits or parts of fruits of said variety, or fruits of progeny thereof, or fruits of a derived variety.

In another embodiment the plant, plant part or seed of NUN 70048 PPH is inside a container, For example, containers such as cans, boxes, crates, bags, cartons, Modified Atmosphere Packaging, films (e.g. biodegradable films), etc. comprising a plant or a part of a plant (fresh and/or processed) of NUN 70048 PPH or a seed of NUN 70048 PPH are also provided herein. In a preferred embodiment, the container comprises a plurality of seeds of NUN 70048 PPH, or a plurality of plant parts of NUN 70048 PPH.

The present invention further relates to a pepper variety, referred to as NUN 70048 PPH, which—when compared to its REFERENCE VARIETY 5810—has the following distinguishing characteristics: 1) Average fruit length; 2) Average fruit diameter at mid-point; 3) Average fruit diameter at calyx attachment; 4) Average number of flowers per leaf axil; 5) Typical plant attitude; 6) Average leaf width; 7) Average seed cavity length; 8) Average seed cavity diameter; 9) Average plant width; and 10) Fruit anthocyanin type, where the characteristics are determined at the 5% significance level for plants grown under the same environmental conditions. Also encompassed by the present invention are parts of that plant.

In one embodiment a plant of NUN 70048 PPH or a progeny plant thereof, comprises all of the following morphological and/or physiological characteristics (i.e. average values of distinguishing characteristics, as indicated on the USDA Objective description of variety—pepper (unless indicated otherwise)): 1) Average fruit length; 2) Average fruit diameter at mid-point; 3) Average fruit diameter at calyx attachment; 4) Average number of flowers per leaf axil; 5) Typical plant attitude; 6) Average leaf width; 7) Average seed cavity length; 8) Average seed cavity diameter; 9) Average plant width; and 10) Fruit anthocyanin type, where the characteristics are determined at the 5% significance level for plants grown under the same environmental conditions. An example of values for the distinguishing characteristics collected in a trial run according to UDSA requirements can be found in Table 1. A part of this plant is also provided.

The invention further provides a pepper plant which does not differ from the plant of NUN 70048 PPH as determined at the 1%, 2%, 3%, 4% or 5% significance level when grown under the same environmental conditions. Thus the plants are measured in the same trial. Preferably, the trial is conducted as recommended by the USDA or UPOV. The invention also comprises a part of said plant The invention also provides a tissue or cell culture comprising cells of NUN 70048 PPH. Such a tissue culture can for example be grown on plates or in liquid culture, or be frozen for long term storage. The cells of NUN 70048 PPH used to start the culture can be selected from any plant part suitable for vegetative reproduction, or in a preferred embodiment can be selected from embryos, meristems, cotyledons, hypocotyl, pollen, leaves, anthers, roots, root tips, pistil, petiole, flower, fruit, seed, stem and stalks of NUN 70048 PPH. In another preferred embodiment, the tissue culture does not contain somaclonal variation or has reduced somaclonal variation. The skilled person is familiar with methods to reduce or prevent somaclonal variation, including regular reinitiation.

In one embodiment the invention provides a pepper plant regenerated from the tissue or cell culture of NUN 70048 PPH, wherein the regenerated plant is not significantly different from NUN 70048 PPH in all, or all but one, two or three, of the physiological and morphological characteristics (determined at the 5% significance level when grown under the same environmental conditions). Optionally, the plant has one, two or three the physiological and morphological characteristics that are affected by a mutation or by transformation. In another embodiment, the invention provides a pepper plant regenerated from the tissue or cell culture of NUN 70048 PPH, wherein the plant has all of the physiological and morphological characteristics of said variety determined at the 5% significance level when grown under the same environmental conditions. In these cases, similarity or difference of a characteristic is determined by measuring the characteristics of a representative number of plants grown under the same environmental conditions, determining whether type/degree characteristics are the same or different and determining whether numerical characteristics are significantly different (determined at the 5% significance level).

A pepper according to the invention, such as NUN 70048 PPH, or its progeny, or a plant having all physiological and/or morphological characteristics but one, two or three which are different from those of NUN 70048 PPH, can also be reproduced using vegetative reproduction methods. Therefore, the invention provides for a method of producing a plant, or a part thereof, of variety NUN 70048 PPH, comprising vegetative propagation of said variety. Vegetative propagation comprises regenerating a whole plant from a plant part of variety NUN 70048 PPH (or from a progeny of said variety or from or a plant having all physiological and/or morphological characteristics of said variety but one, two or three different characteristics), such as a cutting, a cell culture or a tissue culture.

The invention also concerns methods of vegetatively propagating a part of the plant of the invention NUN 70048 PPH. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets. Therefore, the method also comprises regenerating a whole plant from said part of NUN 70048 PPH.

In a preferred embodiment, the part of the plant to be propagated is is a cutting, a cell culture or a tissue culture.

The invention also provides for a vegetatively propagated plant of variety NUN 70048 PPH (or from progeny of said variety or from or a plant having all but one, two or three physiological and/or morphological characteristics of NUN 70048 PPH) wherein the plant has all of the morphological and physiological characteristics of NUN 70048 PPH when the characteristics are determined at the 5% significance level for plants grown under the same conditions. In another embodiment, the propagated plant has all but one, two or three of the morphological and physiological characteristics of NUN 70048 PPH when the characteristics are determined at the 5% significance level for plants grown under the same conditions. A part of said propagated plant or said propagated plant with one, two or three differences is also included.

In an embodiment, the invention provides a method for producing a pepper plant part, preferably a fruit, comprising the steps of:
  a. Growing a plant of NUN 70048 PPH until it sets at least one fruit
  b. Collecting the fruit of step a)
Preferably, the fruit is collected at harvest maturity. In another embodiment, the fruit is collected when the seed is ripe. A plant of NUN 70048 PPH can be produced by seeding directly in the soil (e.g., field) or by germinating the seeds in controlled environment conditions (e.g., greenhouses) and optionally then transplanting the seedlings into the field. For example, the seed can be sown into prepared seed beds where they will remain for the entire production the crop. Pepper can also be grown entirely in greenhouses In still another aspect the invention provides a method of producing a pepper plant, comprising crossing a plant of pepper NUN 70048 PPH with a second pepper plant at least once, allowing seed to develop and optionally harvesting said progeny seed. The skilled person can select progeny from said crossing. Optionally, the progeny is crossed twice, thrice, or four, five, six or seven times, and allowed to set seed. In one embodiment of the invention, the first step in "crossing" comprises planting seeds of a first and a second parent pepper plant, often in proximity so that pollination will occur; for example, mediated by insect vectors. Alternatively, pollen can be transferred manually. Where the plant is self-pollinated, pollination may occur without the need for direct human intervention other than plant cultivation. After pollination the plant can produce seed.

In yet another aspect the invention provides a method of producing a plant, comprising selfing a plant of variety NUN 70048 PPH one or more times, and selecting a progeny plant from said selfing. In one aspect the progeny plant retains all the distinguishing characteristics of NUN 70048 PPH described above. In a different embodiment the progeny plant comprises all (or all but one, two or three) of the physiological and morphological characteristic of NUN 70048 PPH of Table 1, and/or Table 2. In a further embodiment the progeny plant comprises all physiological and morphological characteristic of NUN 70048 PPH when grown under the same environmental conditions.

In other aspects, the invention provides a progeny plant of variety NUN 70048 PPH such as a progeny plant obtained by further breeding that variety. Further breeding with the variety of the invention includes selfing that variety one or more times and/or cross-pollinating that variety with another pepper plant or variety one or more times. In particular, the invention provides for a progeny plant that retains all the essential morphological and physiological characteristics of NUN 70048 PPH or, in another embodiment, a progeny plant that retains all, or all but one, two or three, of the morphological and physiological characteristics of NUN 70048 PPH, optionally all or all but one, two or three of the characteristics as listed in Table 1 and/or 2, when grown under the same environmental conditions, determined at the 5% significance level for numerical characteristics. In a preferred embodiment, the progeny is a first generation progeny, i.e. the ovule or the pollen (or both) used in the crossing is an ovule or pollen of variety NUN 70048 PPH, i.e. the pollen comes from an anther of NUN 70048 PPH and the ovule comes from an ovary of NUN 70048 PPH. In another aspect, the invention provides for a vegetative reproduction of the variety and a plant having all, or all but 1, 2, or 3 of the physiological and morphological characteristics of NUN 70048 PPH (e.g. as listed in Table 1 and/or 2).

The invention also provides a method for collecting pollen of NUN 70048 PPH, comprising the steps of:
 a. Growing a plant of NUN 70048 PPH until at least one flower contains pollen
 b. Collecting the pollen of step a)

Preferably, the pollen is collected when it is mature or ripe. A suitable method for collecting pollen comprises collecting anthers or the part of the anther that contains pollen, for example by cutting it off. Pollen can be collected in containers. Optionally, collected pollen can be used to pollinate a pepper flower.

The morphological and/or physiological differences between two different individual plants of the invention (e.g. between NUN 70048 PPH and a progeny of NUN 70048 PPH) or between a plant of NUN 70048 PPH or progeny of said variety, or a plant having all, or all but 1, 2, or 3, of the physiological and morphological characteristics of NUN 70048 PPH (or all, or all but 1, 2, or 3 of the characteristics as listed in Table 1 and/or 2) and another known variety can easily be established by growing said variety next to each other or next to the other variety (in the same field, under the same environmental conditions), preferably in several locations which are suitable for said pepper cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA, whereby various characteristics, for example maturity, days from seeding to harvest, plant habit, plant attitude, leaf shape, leaf color, blistering, numbers of flowers per leaf axil, number of calyx lobes, number of petals, fruit group, immature fruit color, mature fruit color, pungency, flavor, fruit glossiness, fruit size, fruit shape, average number of fruits per plant, seed size, seed weight, anthocyanin level, disease resistance, insect resistance, can be measured and directly compared for species of pepper. Thus, the invention comprises pepper plant having one, two or three physiological and/or morphological characteristics which are different from those of the plant of NUN 70048 PPH and which otherwise has all the physiological and morphological characteristics of the plant of NUN 70048 PPH, when determined at the 5% significance level for plants grown under the same environmental conditions. In a preferred embodiment, the different characteristic is affected by a mutation, optionally induced mutation, or by transformation.

The morphological and physiological characteristics (and the distinguishing characteristics) of NUN 70048 PPH are provided in the Examples, in Table 1 and/or 2. Encompassed herein is also a plant obtainable from NUN 70048 PPH (e.g. by selfing and/or crossing and/or backcrossing with said variety and/or progeny of said variety) comprising all or all but one, two or three of the physiological and morphological characteristics of NUN 70048 PPH listed in Table 1 and/or 2 as determined at the 5% significance level for numerical characteristics or identical for non-numerical characteristics when grown under the same environmental conditions and/or comprising one or more (or all; or all except one, two or three) characteristics when grown under the same environmental conditions.

Also at-harvest and/or post-harvest characteristics of fruits can be compared, such as cold storage holding quality, post-harvest flesh firmness, and Brix can be measured using known methods. (Fruit) Flesh firmness can for example be measured using a penetrometer, e.g. by inserting a probe into the fruit flesh and determining the insertion force, or by other methods. Fruit flesh firmness can for example be measured using a "FT 327 Penetrometer", available from QA Supplies LLC, 1185 Pineridge Road, Norfolk, Va. 23502.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (World Wide Web at rhs.org.uk/Plants/RHS-Publications/RHS-colour-charts).

In a preferred embodiment, the invention provides for a pepper fruit of variety NUN 70048 PPH, or a part of a fruit of said varieties. In another embodiment, the invention provides for a container comprising or consisting of a plurality of harvested pepper fruits or parts of fruits of said variety, or fruits of progeny thereof, or fruits of a derived variety.

In yet a further embodiment, the invention provides for a method of producing a new pepper plant. The method comprises crossing a plant of the invention i.e. NUN 70048 PPH, or a plant comprising all but 1, 2, or 3 of the morphological and physiological characteristics of said variety (as listed in Table 1 and/or 2), or a progeny plant thereof, either as male or as female parent, with a second pepper plant (or a wild relative of pepper) one or more times, and/or selfing a pepper plant according to the invention i.e. NUN 70048 PPH, or a progeny plant thereof, one or more times, and selecting progeny from said crossing and/or selfing. The second pepper plant may for example be a line or variety of the species *Capsicum annuum, C. frutecens, C. baccatum, C. chinense*, or other *Capsicum* species.

The invention provides for methods of producing plants which retain all the morphological and physiological characteristics of a plant of the invention i.e. NUN 70048 PPH. The invention provides also for methods of producing a plant comprising all but 1, 2, or 3 or more of the morphological and physiological characteristics of NUN 70048 PPH (e.g. as listed in Table 1 and/or 2), but which are still genetically closely related to said variety. The relatedness can, for example be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to NUN 70048 PPH if its DNA fingerprint is at least 80%, 90%, 95% or 98% identical to the fingerprint of NUN 70048 PPH. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Parvathaneni et al., J. Crop Sci. Biotech. 2011 (Mar.) 14 (1): 39-43).

The invention also provides a plant and a variety obtained or selected by applying these methods on NUN 70048 PPH. Such a plant may be produced by crossing and/or selfing, or alternatively, a plant may simply be identified and selected amongst plants of said variety, or progeny of said variety, e.g. by identifying a variant within NUN 70048 PPH or within progeny of said variety (e.g. produced by selfing) which variant differs from NUN 70048 PPH in one, two or three of the morphological and/or physiological characteristics (e.g. in one, two or three distinguishing characteristics), e.g. those listed in Table 1 and/or 2 or others. In one embodiment the invention provides a pepper plant having a Jaccard's Similarity index with NUN 70048 PPH of at least 0.8, e.g. at least 0.85, 0.9, 0.95, 0.98 or even at least 0.99.

WO2013182646, which is incorporated by reference, relates to a non-destructive method for analyzing maternal DNA of a seed. In this method the DNA is dislodged from the seed coat surface and can be used to collect information on the genome of the maternal parent of the seed. This method for analyzing maternal DNA of a seed comprises the steps of contacting a seed with a fluid to dislodge DNA from the seed coat surface, and analyzing the DNA thus dislodged from the seed coat surface using methods known in the art. The skilled person is thus able to determine whether a seed has grown on a plant of a plant of the invention i.e. NUN 70048 PPH is a progeny of said variety, because the seed coat of the seed is a maternal tissue genetically identical to NUN 70048 PPH. In one embodiment, the present invention relates to a seed coat comprising maternal tissue of NUN 70048 PPH. In another embodiment the invention relates to a pepper seed comprising a maternal tissue of NUN 70048 PPH.

By crossing and/or selfing also (one or more) single traits may be introduced into the variety of the invention i.e. NUN 70048 PPH (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g. dominant or recessive) and one or more QTLs (quantitative trait loci) may be transferred into NUN 70048 PPH by breeding with said variety.

Alternatively, a single trait converted plant or single locus converted plant of NUN 70048 PPH may be produced by the following steps
 a. obtaining a cell or tissue culture of cells of NUN 70048 PPH;
 b. genetically transforming or mutating said cells;
 c. growing the cells into a plant; and
 d. optionally selecting a plant that contains the desired single locus conversion The skilled person is familiar with various techniques for genetically transforming a single locus in a plant cell, or mutating said cells.

Any pest or disease resistance genes may be introduced into a plant according to the invention, i.e. NUN 70048 PPH, progeny of said variety or into a plant comprising all but 1, 2, or 3 or more of the morphological and physiological characteristics of NUN 70048 PPH (e.g. as listed in Table 1). Resistance to one or more of the following diseases or pests is preferably introduced into plants of the invention: Cucumber Mosaic Virus, Curly Top Virus, Pepper Mottle Virus, Potato Y Virus, Tobacco Etch Virus, Tobacco Mosaic Virus, Anthracnose (*Gloeosporium piperatum*), Bacterial Spot (*Xanthomonas vesicatoria*), Cercospora Leaf Spot (*Cercospora capsici*), Nematode (*Meloidogyne incognita acrita*), Phytophthora Root Rot (*Phytophthora capsici*), Ripe Rot (*Vermicularia capsici*), Southern Blight (*Sclerotium rolfsii*) and/or Verticillium Wilt (*Verticillium dahliae*). Other resistance genes, against pathogenic viruses, fungi, bacteria, nematodes, insects or other pests may also be introduced. In an embodiment, the resistance is TSWV resistance.

Thus, invention also provides a method for developing a pepper plant in a pepper breeding program, using a pepper plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 70048 PPH or progeny of said variety, or a plant comprising all but 1, 2, or 3 or more of the morphological and physiological characteristics of NUN 70048 PPH (e.g. as listed in Table 1 and/or 2), with a different pepper plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Martin et al. 2008, Australian Journal of Crop Science 1(2): 43-46). For breeding methods in general see Principles of Plant Genetics and Breeding, 2007, George Acquaah, Blackwell Publishing, ISBN-13: 978-1-4051-3646-4.

The invention also provides a pepper plant comprising at least a first set of the chromosomes of pepper variety NUN 70048 PPH, a sample of seed of said variety is deposited under Accession Number NCIMB 43509; optionally further comprising a single locus conversion or a mutation, wherein said plant has essentially all of the morphological and physiological characteristics of the plant comprising at least a first set of the chromosomes of said variety. In another embodiment, this single locus conversion confers a trait selected from the group consisting of yield, storage properties, color, male sterility, herbicide tolerance, insect resistance, pest resistance, disease resistance, environmental stress tolerance, modified carbohydrate metabolism and modified protein metabolism.

In one embodiment, a plant according to the invention, i.e. NUN 70048 PPH may also be mutated (by e.g. irradiation, chemical mutagenesis, heat treatment, etc.) and mutated seeds or plants may be selected in order to change one or more characteristics of said variety. Methods such as TILLING may be applied to pepper populations in order to identify mutants. Similarly, NUN 70048 PPH may be transformed and regenerated, whereby one or more chimeric genes are introduced into the variety or into a plant comprising all but 1, 2, 3, or more of the morphological and physiological characteristics (e.g. as listed in Table 1 and/or 2). Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 70048 PPH, or progeny of said variety, by transforming said variety or progeny of said variety with a transgene that confers the desired trait, wherein the transformed plant retains all or all but one, two or three of the phenotypic and/or morphological and/or physiological characteristics of NUN 70048 PPH or the progeny of said variety and contains the desired trait.

The invention also provides a plant or a cell of a plant comprising a desired trait produced by mutating a plant of variety NUN 70048 PPH or a cell thereof and selecting a plant the desired trait, wherein the mutated plant retains all or all but one of the phenotypic and morphological characteristics of said variety, optionally as described for each variety in in Table 1 and/or 2, and contains the desired trait and wherein a representative sample of seed of variety NUN 70048 PPH is deposited under Accession Number NCIMB 43509. In a further embodiment, the desired trait is selected from the group consisting of yield, compact pepper, fruit quality, male sterility, herbicide tolerance, insect resistance, pest resistance, disease resistance, Powdery mildew resistance without necrosis, environmental stress tolerance, modified carbohydrate metabolism, modified protein metabolism and ripening.

A suitable method for inducing mutation in NUN 70048 PPH comprises the steps of:
  a. Exposing a seed, a plant or a plant part or a cell of NUN 70048 PPH to a mutagenic chemical or to radiation, wherein a representative sample of seed of NUN 70048 PPH is deposited under Accession Number NCIMB 43509,
  b. Selecting a seed, a plant or a plant part or a cell of NUN 70048 PPH having a mutation
  c. Optionally growing and/or multiplying the seed, plant or plant part or cell of NUN 70048 PPH of step b) having the mutation.

The invention also provides a plant having one, two or three physiological and/or morphological characteristics which are different from those of NUN 70048 PPH and which otherwise has all the physiological and morphological characteristics of said variety, wherein a representative sample of seed of variety NUN 70048 PPH is deposited under Accession Number NCIMB 43509. In particular variants which differ from NUN 70048 PPH in none, one, two or three of the characteristics mentioned in Table 1 and/or 2 are encompassed.

A part of a variety of the invention, i.e. NUN 70048 PPH (or of progeny of said varieties or of a plant having all physiological and/or morphological characteristics but one, two or three which are different from those of said variety) encompasses any cells, tissues, organs obtainable from the seedlings or plants, such as but not limited to: a pepper fruit or a part thereof, a cutting, hypocotyl, cotyledon, seed coat, pollen and the like. Such parts can be stored and/or processed further. Encompassed are therefore also food or feed products comprising a part of NUN 70048 PPH or a part of progeny of said varieties, or a part of a plant having all but one, two or three physiological and/or morphological characteristics of NUN 70048 PPH, comprising one or more of such parts, optionally processed (such as canned, chopped, cooked, roasted, in a sauce, in a sandwich, pasted, puréed or concentrated, juiced, frozen, dried, pickled, or powdered).

In one aspect a haploid plant and/or a doubled haploid plant of NUN 70048 PPH, or of a plant having all but one, two or three physiological and/or morphological characteristics of NUN 70048 PPH, or progeny of any of these, is encompassed herein. Haploid and doubled haploid (DH) plants can, for example, be produced by cell or tissue culture and chromosome doubling agents and regeneration into a whole plant. For DH production chromosome doubling may be induced using known methods, such as colchicine treatment or the like.

In yet another aspect haploid plants and/or doubled haploid plants derived from NUN 70048 PPH that, when combined, make a set of parents of NUN 70048 PPH are encompassed herein. Thus the haploid plant and/or the doubled haploid plant of NUN 70048 PPH can be used in a method for generating parental lines of NUN 70048 PPH.

Using methods known in the art like "reverse synthesis of breeding lines" or "reverse breeding", it is possible to produce parental lines for a hybrid plant such as NUN 70048 PPH; where normally the hybrid is produced from the parental lines. Thus, this method introduces a tool that was not available in traditional breeding; a skilled person can take any individual heterozygous plant (called a "phenotypically superior plant" in Example 2 of WO2014076249; NUN 70048 PPH is such a plant) and generate a combination of parental hues (reverse breeding parental lines) that, when crossed, produce the variety NUN 70048 PPH. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014076249 or from Wijnker et al., Nature Protocols Volume: 9, Pages: 761-772(2014) DOI:doi:1038/nprot.2014.049 . Such method for producing parental lines for a hybrid organism, comprises the steps of:

a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B); d) selecting at least one, pair of doubled haploid lines that have complementary alleles for at least a subset of the genetic markers, wherein each member of the pair is suitable as a parental line for a hybrid organism.

Thus in one aspect, the invention relates to a method of producing a combination of parental lines of a plant of the invention (NUN 70048 PPH) comprising the step of making doubled haploid cells from haploid cells from said plant or a seed of that plant; and optionally crossing these parental lines to produce and collect seeds. In another aspect, the invention relates to a combination of parental lines produced by this method. In still another aspect said combination of parental lines can be used to produce a seed or plant of NUN 70048 PPH when these parental lines are crossed. In still another aspect, the invention relates to a combination of parental lines from which a seed or plant having all physiological and/or morphological characteristics of NUN 70048 PPH (when the characteristics are determined at the 5% significance level for plants grown under the same conditions).

In another aspect, the invention comprises a method for making doubled haploid cells from haploid cells of NUN 70048 PPH according to various methods known to the skilled person. A suitable method is colchicine treatment.

In another alternative aspect, the invention provides a method of introducing a single locus conversion or single trait conversion or a desired trait into NUN 70048 PPH comprising:
  a. obtain a combination of a parental lines of NUN 70048 PPH, optionally through reverse synthesis of breeding lines,
  b. introduce a single locus conversion in at least one of the parents of step a;
  c. crossing the converted parent with the other parent of step a to obtain seed of NUN 70048 PPH A combination of a male and a female parental line of NUN 70048 PPH can be generated by methods described herein, for example through reverse synthesis of breeding lines.

In an embodiment of the invention, Step b) of the above method—introduce a single locus conversion in at least one of the parents of step a—may be done through the following method:
  i. obtaining a cell or tissue culture of cells of the parental line of NUN 70048 PPH;
  ii. genetically transforming or mutating said cells;
  iii. growing the cells into a plant; and
  iv. optionally selecting plants that contain the single locus conversion, the single trait conversion or the desired trait.

In another embodiment of the invention, Step b) of the above method—introduce a single locus conversion in at least one of the parents of step a—may also be done through the following method:
  i. crossing the parental line of NUN 70048 PPH with a second pepper plant comprising the single locus conversion, the single trait conversion or the desired trait;
  ii. selecting F1 progeny plants that contain the single locus conversion, the single trait conversion or the desired trait;
  iii. crossing said selected progeny plants of step ii with the parental line of step i, to produce a backcross progeny plant;
  iv. selecting backcross progeny plants comprising the single locus conversion, the single trait conversion or the desired trait and otherwise all or all but one, two or three of the morphological and physiological characteristics the parental line of step i to produce selected backcross progeny plants; and
  v. optionally repeating steps iii and iv one or more times in succession to produce selected second, third or fourth or higher backcross progeny plants comprising the single locus conversion, the single trait conversion or the desired trait and otherwise all or all but one, two or three of the morphological and physiological characteristics the parental line of step i to produce selected backcross progeny plants, when grown in the same environmental conditions.

The invention further relates to plants obtained by this method.

The above method is provided, wherein the single locus conversion concerns a trait, wherein the trait is yield or pest resistance or disease resistance. In one embodiment the trait is disease resistance and the resistance is conferred to Cucumber Mosaic Virus, Curly Top Virus, Pepper Mottle Virus, Potato Y Virus, Tobacco Etch Virus, Tobacco Mosaic Virus, Anthracnose (*Gloeosporium piperatum*), Bacterial Spot (*Xanthomonas vesicatoria*), *Cercospora* Leaf Spot (*Cercospora capsici*), Nematode (*Meloidogyne incognita acrita*), *Phytophthora* Root Rot (*Phytophthora capsici*), Ripe Rot (*Vermicularia capsici*), Southern Blight (*Sclerotium rolfsii*) and/or *Verticillium* Wilt (*Verticillium dahliae*). Other resistance genes, against pathogenic viruses, fungi, bacteria, nematodes, insects or other pests may also be introduced. In an embodiment, the resistance is TSWV resistance.

Thus, the invention also provides a combination of parental lines which, when crossed, produce a seed or plant having all physiological and/or morphological characteristics of NUN 70048 PPH but one, two or three which are different (when grown under the same environmental conditions), as well as a seed or plant having all physiological and/or morphological characteristics of NUN 70048 PPH but one, two or three which are different (when the characteristics are determined at the 5% significance level for plants grown under the same conditions).

Also provided is a plant part obtainable from variety NUN 70048 PPH or from progeny of said variety or from a plant having all but one, two or three physiological and/or morphological characteristics which are different from those of NUN 70048 PPH, or from a vegetatively propagated plant of NUN 70048 PPH (or from its progeny or from a plant having all or all but one, two or three physiological and/or morphological characteristics which are different from those of NUN 70048 PPH), being selected from the group consisting of a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed-coat or another maternal tissue which is part of a seed grown on NUN 70048 PPH, or hypocotyl, cotyledon, a scion, a stock, a rootstock, a pistil, an anther, and a flower or a part thereof.

In still yet another aspect, the invention provides a method of determining the genotype of a plant of the invention comprising the step of detecting in the genome (e.g., a sample of nucleic acids) of the plant at least a first polymorphism or an allele. The skilled person is familiar with many suitable methods of genotyping, detecting a polymorphism or detecting an allele including restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium The invention also provides for a food or feed product comprising or consisting of a plant part described herein wherein the plant part can be identified as a part of the plant of the invention. Preferably, the plant part is a pepper fruit or part thereof and/or an extract from a fruit or another plant part described herein. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

Marketable pepper fruits are generally sorted by size and quality after harvest. Alternatively the pepper fruits can be sorted by expected shelf life, pH or Brix.

Peppers may also be grown for use as rootstocks (stocks) or scions (cions). Typically, different types of peppers are grafted to enhance disease resistance, which is usually conferred by the rootstock, while retaining the horticultural qualities usually conferred by the scion. It is not uncommon for grafting to occur between cultivated pepper varieties and related pepper species. Methods of grafting and vegetative propagation are well-known in the art.

So in one aspect the invention relates to a plant comprising a rootstock or scion of NUN 70048 PPH.

All documents (e.g., patent publications) are herein incorporated by reference in their entirety.

CITED REFERENCES

U.S. Pat. No. 8,492,619;
US20060037100;
WO201307831;
WO2014076249;
Acquaah, Principles of Plant Genetics and Breeding, 2007, Blackwell Publishing, ISBN-13: 978-1-4051-3646-4.
Kothari et al., (2010) Biotechnology Advances 28: 35-48;
Martin et al. 2008, Australian Journal of Crop Science 1(2): 43-46
Parvathaneni et al., J. Crop Sci. Biotech. 2011 (Mar.) 14 (1): 39~43);
Sang-Gu et al. (1988), Plant Cell, Tissue and Organ Culture 12: 67-74;
Tiwari et al., BMC Plant Biology 201111:143 DOI: 10.1186/1471-2229-11-143
Vos et al. 1995, Nucleic Acid Research 23: 4407-4414
Wijnker et al., Nature Protocols Volume: 9, Pages: 761-772 (2014) DOI: doi:10.1038/nprot.2014.049
Guidelines for the Conduct of Tests for Distinctness, Uniformity and Stability, TG/76/8 (Geneva, 2006—updated 2015); world wide web at upov.int/under edocs/tgdocs/en/tg076.pdf
(Objective description of variety *Capsicum* spp.) US Department of Agriculture, Agricultural Marketing Service, Plant Variety Protection Office, Beltsville, Md. 20705 (world wide web atams.usda.gov/sites/default/files/media/56-Pepper.pdf

EXAMPLES

Development of NUN 70048 PPH

The hybrid NUN 70048 PPH was developed from a male and female proprietary inbred line of Nunhems. The female and male parents were crossed to produce hybrid (F1) seeds of NUN 70048 PPH The seeds of NUN 70048 PPH can be grown to produce hybrid plants and parts thereof (e.g. pepper fruit). The hybrid NUN 70048 PPH can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant has concluded that NUN 70048 PPH is uniform and stable.

Deposit Information

A total of 2500 seeds of the hybrid variety NUN 70048 PPH will be deposited according to the Budapest Treaty by Nunhems B.V. on Nov. 1, 2019, at the NCIMB Ltd., Ferguson Building, Craibstone Estate, Bucksburn, Aberdeen AB21 9YA, United Kingdom (NCIMB). The deposit will be assigned NCIMB number 43509. A deposit of NUN 70048 PPH and of the male and female parent line is also maintained at Nunhems B.V.

Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The most similar variety to NUN 70048 PPH is referred to as Reference Variety, a variety from *Seminis* with the commercial name 5810. In Table 1 a comparison between NUN 70048 PPH and the Reference Variety will be shown based on a trial in the USA during the trial season 2018. Trial location Acampo, Calif., USA (N38.192873, W121.232637), transplanting date: 5 Jul. 2017.

A trial of 40 plants of each variety, from which at least 15 plants or plant parts were randomly selected, will be used to measure characteristics. For numerical characteristics averages will be calculated. For non-numerical characteristics the type/degree will be determined. In Table 1 the USDA descriptors of NUN 70048 PPH (this application) and the Reference Variety (commercial variety) are listed, which will be measured in the trial to be performed.

In accordance with one aspect of the present invention, there is provided a plant having the physiological and morphological characteristics of NUN 70048 PPH as will be presented in Table 1.

TABLE 1

Objective description of varieties NUN 70048 PPH and Reference Variety

| USDA descriptor | Application Variety NUN 70048 PPH | Reference Variety 5810 |
|---|---|---|
| 1. SPECIES: 1 = C. annuum 2 = C. frutescens 3 = C. baccatum 4 = C. chinense 5 = Other (specify) | 1 | 1 |
| 2. MATURITY (In Region of Best Adaptability): | | |
| Days from transplanting until mature green stage | n.r. | n.r. |
| Days from transplanting until mature red or yellow stage | n.r. | n.r. |
| Days from direct seeding until mature green stage | n.r. | n.r. |
| Days from direct seeding until mature red or yellow stage | n.r. | n.r. |
| 3. PLANT | | |
| Plant Habit: 1 = Compact 2 = Semi-spreading 3 = Spreading 4 = Other | 2 | 2 |
| Plant Attitude: 1 = Erect 2 = Semi-erect 3 = Prostrate 4 = Other | 2 | 1 |
| Plant Height (cm) | 54.8 | 60.43 |
| Plant Width (cm) | 63.43 | 54.87 |
| Length of Stem from Cotyledons to First Flower (cm) | 13.07 | 11.97 |
| Length of Third Internode (from soil surface) (mm) | 7.78 | 9.61 |
| Basal Branches: 1 = None 2 = Few (2-3) 3 = Many (more than 3) | n.r. | n.r. |
| Branch Flexibility: 1 = Willowy (Cayenne Long Red) 2 = Rigid (Yolo Wonder L) | 2 | 2 |
| Stem Strength (Breakage Resistance): 1 = Weak 2 = Intermediate 3 = Strong | n.r. | n.r. |
| 4. LEAVES: | | |
| Leaf Width (mm) | 46.83 | 50.64 |
| Leaf Length (mm) | 90.35 | 87.61 |
| Petiole Length (mm) | 37.31 | 38.29 |
| Mature Leaf Shape: 1 = Lanceolate 2 = Elliptic | 2 | 2 |
| Leaf Color: 1 = Light Green 2 = Medium Green 3 = Dark Green 4 = Purple 5 = Other (specify) (RHS color chart value) | n.r. | n.r. |
| Leaf and Stem Pubescence: 1 = Absent (Yolo Wonder L) 2 = Light 3 = Moderate (Serrano) 4 = Heavy (Chili Piquin) | 1 | 1 |
| Margin Undulation: 1 = Absent 2 = V. Weak 3 = Weak 4 = Medium 5 = Strong 6 = V. Strong | 4 | 4 |
| Blistering: 1 = Absent 2 = Very Weak 3 = Weak 4 = Medium 5 = Strong 6 = Very Strong | 1 | 2 |
| 5. FLOWERS: | | |
| Number of Flowers per Leaf Axil | 2.53 | 1.86 |
| Number of Calyx Lobes | 6 | 6 |
| Number of Petals | 6 | 5.87 |
| Flower Diameter (mm) | 19.83 | 18.93 |
| Corolla Color: 1 = White 2 = Purple 3 = Other (Specify) | 1 | 1 |
| Corolla Throat Markings: 1 = Yellow (Tan) 2 = Purple 3 = Other (Specify) | 1 | 1 |
| Anther Color: 1 = Yellow 2 = Purple 3 = Other (Specify) | 2 | 2 |
| Style Length: 1 = Less Than Stamen 2 = Same as Stamen 3 = Exceeds Stamen | 3 | 2 |
| Self-Incompatibility: 1 = Absent 2 = Present | n.r. | n.r. |
| 6. FRUIT: | | |
| Group: 1 = Bell (Yolo Wonder L) 2 = Pimiento (Pimiento Perfection) 3 = Ancho (Mexican Chili) 4 = Anaheim Chili (Sandia) 5 = Cayenne (Cayenne Long Red) 6 = Cuban (Cubanelle) 7 = Jalapeno (Jalapeno) 8 = Small Hot (Serrano) 9 = Cherry (Sweet Cherry) 10 = Short Wax (Floral Gem) 11 = Long Wax (Sweet Banana) 12 = Tabasco (Tabasco) 13 = Habanero (Scotch Bonnet) 14 = Other | 7 | 7 |
| Immature Fruit Color: 1 = Light Green (Cubanelle) 2 = Medium Green (Long Thin Cayenne) 3 = Dark Green (Yolo Wonder L) 4 = Very Dark Green (Ancho Chili) 5 = Yellow (Yellow Belle) 6 = Purple (Violetta) 7 = Ivory (Twiggy) 8 = Other | 3 | 3 |
| Mature Fruit Color: 1 = Red (Yolo Wonder L) 2 = Orange 3 = Orange -Yellow (Golden Calwonder) 4 = Brown (Mulatto) 5 = Ivory 6 = Green (Permagreen) 7 = Salmon 8 = Lemon Yellow 9 = Other | 1 | 1 |
| Pungency: 1 = Sweet (Yolo Wonder L) 2 = Hot (Jalapeno) | 2 | 2 |
| mg Capsaicin per gram dry fruit | n.r. | n.r. |
| Scoville Units (dry fruit) | n.r. | n.r. |

TABLE 1-continued

Objective description of varieties NUN 70048 PPH and Reference Variety

| USDA descriptor | Application Variety NUN 70048 PPH | Reference Variety 5810 |
|---|---|---|
| Flavor: 1 = Mild Pepper Flavor 2 = Moderate Pepper Flavor 3 = Strong Pepper Flavor 4 = Other. | 2 | 2 |
| Fruit Glossiness: 1 = Dull 2 = Moderate 3 = Shiny | 3 | 3 |
| Surface Smoothness: 1 = Smooth (Yolo Wonder L) 2 = Rough (Long Thin Cayenne) | 1 | 1 |
| Fruit Position: 1 = Upright (Santaka) 2 = Horizontal 3 = Pendent (Jalapeno) | 3 | 3 |
| Calyx Shape: 1 = Cup-shaped (Enveloping Fruit Base) 2 = Saucer-shaped (Flat, Non-Enveloping) | 2 | 2 |
| Calyx Diameter (mm) | 21.05 | 24.99 |
| Fruit Length (mm) | 96.21 | 86.91 |
| Fruit Diameter at Calyx Attachment (mm) | 24.79 | 29.9 |
| Fruit Diameter at Mid-point (mm) | 29.59 | 33.15 |
| Flesh Thickness at Mid-point (mm) | 4.09 | 4.51 |
| Average Number of Fruits per Plant | n.r. | n.r. |
| % Large fruits | 26.7 (43 to 60 g) | 60 |
| % Medium fruits | 40 (35 to 42 g) | 6.7 |
| % small fruits | 33.3 (20 to 34 g) | 33.3 |
| Average Fruit Weight (gm) | 37.73 | 42.8 |
| Fruit Base Shape: 1 = Cupped (Yolo Wond L), 2 = Rounded (Jalapeno) | 2 | 2 |
| Fruit Apex Shape: 1 = Pointed (Long Thin Cayenne) 2 = Blunt (Yolo Wonder L) | 2 | 2 |
| Fruit Shape: 1 = Bell (Yolo Wonder L) 2 = Conical (Pimiento) 3 = Elongate (Long Thin Cayenne) 4 = Oblong (Jalapeno) 5 = Oblate (Sunnybrook) 6 = Globe (Red Cherry) 7 = Other | 4 | 4 |
| Fruit Shape (Longitudinal Section, see attached pictures): 1 = Flattened 2 = Round 3 = Heart-shaped 4 = Square 5 = Rectangular 6 = Trapezoid 7 = Narrow Triangular 8 = Triangular 9 = Horn-shaped | 5 | 5 |
| Fruit Shape (Cross Section, at Level of Placenta): 1 = Elliptic 2 = Triangular 3 = Quadrangular 4 = Circular | 4 | 4 |
| Fruit Set: 1 = Scattered 2 = Concentrated | 1 | 1 |
| Interloculary Grooves: 1 = Absent 2 = Very Shallow 3 = Shallow 4 = Medium 5 = Deep 6 = Very Deep | 1 | 1 |
| % Fruits with one locule | 0 | 0 |
| % Fruits with two locules | 0 | 0 |
| % Fruits with three locules | 66.7 | 40 |
| % Fruits with four locules | 33.3 | 60 |
| % Fruits with five or more locules | 0 | 0 |
| Average Number of Locules | 3.33 | 3.63 |
| Pedicel Length (mm) | 35.17 | 33.22 |
| Pedicel Thickness (mm) | 4.89 | 5.72 |
| Pedicel Shape: 1 = Straight 2 = Curved | 2 | 2 |
| Pedicel Cavity: 1 = Absent 2 = Present | 1 | 1 |
| 7 SEED: | | |
| Seed Cavity Length (mm) | 76.78 | 69.32 |
| Seed Cavity Diameter (mm) | 22.08 | 26.74 |
| Placenta Length (mm) | 25.51 | 34.82 |
| Number of Seeds per Fruit | 135.13 | 130.13 |
| Gm per 1000 seeds | n.r. | n.r. |
| Seed Color 1 = Yellow; 2 = Purple | 1 | 1 |
| 8. ANTHOCYANIN (1 = Absent; 2 = Weak; 3 = Moderate; 4 = Strong): | | |
| Seedling hypocotyl | n.r. | n.r. |
| Stem | 2 | 1 |
| Node | 3 | 4 |
| Leaf | 1 | 1 |
| Pedicel | 1 | 1 |
| Calyx | 1 | 1 |
| Fruit | 4 | 2 |

TABLE 2

| Non - USDA descriptor | Application Variety NUN 70048 PPH | Reference Variety 5810 |
|---|---|---|
| Petiole diameter (mm) | 1.95 | 1.8 |

Table 1 and 2 contain typical values. Values may vary due to environment. Other values that are substantially equivalent are also within the scope of the invention. N.A.=not applicable; n.r.=not recorded.

What is claimed is:

1. A plant, plant part or seed of pepper variety NUN 70048 PPH, wherein a representative sample of seed of said pepper variety is deposited under Accession Number NCIMB 43509.

2. The plant part of claim 1, wherein the plant part is a leaf, pollen, an ovule, a fruit, a scion, a root, a rootstock, cutting, flower, or a cell.

3. A seed that produces the plant of claim 1.

4. A seed grown on the plant of claim 1.

5. A pepper plant or a part thereof, having all of the physiological and morphological characteristics of the plant of claim 1.

6. A pepper plant or a part thereof which does not differ from the plant of claim 1, when the numerical characteristics are determined at the 5% significance level when grown under the same environmental conditions, and wherein a representative sample of seed of said pepper variety NUN 70048 PPH is deposited under Accession Number NCIMB 43509.

7. A tissue or cell culture comprising regenerable cells of the plant or plant part of claim 1, wherein said cells are derived from said pepper variety NUN 70048 PPH, and suitable for regenerating into a plant having all of the physiological and morphological characteristics of pepper variety NUN 70048 PPH.

8. The tissue or cell culture according to claim 7, comprising cells or protoplasts derived from a plant part, wherein the plant part is a meristem, a cotyledon, a hypocotyl, pollen, a leaf, an anther, a root, a root tip, a pistil, a petiole, a flower, a fruit, a stem, or a stalk.

9. A pepper plant regenerated from the tissue or cell culture of claim 7, wherein the plant has all of the, physiological and morphological characteristics of the plant of variety NUN 70048 PPH, when the numerical characteristics are determined at the 5% significance level for plants grown under the same environmental conditions, and wherein a representative sample of seed of pepper variety NUN 70048 PPH is deposited under Accession Number NCIMB 43509.

10. A method of producing the plant of claim 1, said method comprising vegetative propagation of at least a part of the plant of variety NUN 70048, wherein a representative sample of seed of said pepper variety is deposited under Accession Number NCIMB 43509.

11. The method of claim 10, wherein said vegetative propagation comprises regenerating a whole plant from said part of the plant of variety NUN 70048 PPH, wherein a representative sample of seed of said pepper variety is deposited under Accession Number NCIMB 43509.

12. The method of claim 10, wherein said part is a cutting, a cell culture or a tissue culture.

13. A vegetatively propagated plant of claim 1, or a part thereof, wherein the vegetatively propagated plant has all of the physiological and morphological characteristics of the plant of variety NUN 70048 PPH, when the numerical characteristics are determined at the 5% significance level for plants grown under the same environmental conditions, and wherein a representative sample of seed of pepper variety NUN 70048 PPH is deposited under Accession Number NCIMB 43509.

14. A method of producing a pepper plant, comprising crossing the plant of claim 1 with a second pepper plant at least once, and selecting a progeny pepper plant from said crossing and optionally allowing the progeny pepper plant to form seed, wherein said selected progeny pepper plant has all of the physiological and morphological characteristics of the plant of variety NUN 70048 PPH when grown under the same environmental conditions, and wherein a representative sample of said pepper variety is deposited under Accession Number NCIMB 43509.

15. A plant of pepper variety NUN 70048 PPH further comprising a single locus conversion, wherein said plant has all of the morphological and physiological characteristics of the plant of variety NUN 70048 PPH, wherein a representative sample of seed of said pepper variety is deposited under Accession Number NCIMB 43509, when the numerical characteristics are determined at the 5% significance level for plants grown under the same environmental conditions, wherein the single locus conversion confers a trait male sterility, herbicide tolerance, insect resistance, pest resistance, disease resistance, environmental stress tolerance, modified carbohydrate metabolism, or modified protein metabolism.

16. A method of making double haploid cells of pepper variety NUN 70048 PPH, said method comprising making doubled haploid cells from haploid cells from the plant or seed of pepper variety NUN 70048 PPH, wherein a representative sample of seed of pepper variety NUN 70048 PPH is deposited under Accession Number NCIMB 43509.

17. A plant comprising the scion or rootstock of claim 2.

18. A container comprising the plant, plant part or seed of claim 1.

19. A food or a feed product or a processed product comprising the plant part of claim 2, wherein the plant part comprises at least one cell of pepper variety NUN 70048 PPH.

20. A method of producing a pepper fruit, said method comprising
   a. growing the plant of claim 1 until it sets at least one fruit; and
   b. collecting the fruit of step a).

21. A method for collecting pollen of the plant of variety NUN 70048 PPH, said method comprising:
   a. growing the plant of claim 1 until at least one flower contains pollen; and
   b. collecting the pollen of step a).

22. A method of producing a pepper plant having a desired trait, said method comprising mutating a plant or plant part of pepper variety NUN 70048 PPH and selecting a mutated plant with the desired trait, wherein the mutated plant contains the desired trait and has all of the physiological and morphological characteristics of pepper variety NUN 70048 PPH, and wherein a representative sample of seed of said pepper variety is deposited under Accession Number NCIMB 43509.

23. The method of claim 22, where the desired trait is fruit quality, male sterility, herbicide tolerance, insect resistance, pest resistance, disease resistance, virus resistance, TSWV resistance, environmental stress tolerance, modified carbohydrate metabolism, modified protein metabolism, or ripening.

* * * * *